United States Patent
Randall et al.

[11] Patent Number: 6,114,350
[45] Date of Patent: Sep. 5, 2000

[54] CYANINE DYES AND SYNTHESIS METHODS THEREOF

[75] Inventors: Malcolm Harry Randall, Wayland; Philip Richard Buzby, Brockton; Thomas Joseph Erickson, Carlisle; Joseph David Trometer, Framingham; Joseph John Miller, Jr., Dracut; David George Ahern; Mark Norman Bobrow, both of Lexington, all of Mass.

[73] Assignee: NEN Life Science Products, Inc., Boston, Mass.

[21] Appl. No.: 09/294,678

[22] Filed: Apr. 19, 1999

[51] Int. Cl.[7] .................. A61K 31/47; A61K 31/425; C07D 279/16; C07D 215/04; C07D 277/60
[52] U.S. Cl. .................. 514/311; 514/224.2; 514/230.5; 514/249; 514/367; 514/375; 514/394; 514/415; 546/181; 548/465; 548/304.4; 548/152; 548/179; 548/217; 544/51; 544/105; 544/353
[58] Field of Search .................. 548/165, 304.4, 548/152, 179, 217; 546/181; 544/51, 353, 105; 514/224.2, 230.5, 249, 311, 367, 375, 394, 415

[56] References Cited

U.S. PATENT DOCUMENTS

| | | | |
|---|---|---|---|
| 4,138,551 | 2/1979 | Steiger et al. | 542/435 |
| 4,981,977 | 1/1991 | Southwick et al. | 548/455 |
| 5,106,990 | 4/1992 | Ohno et al. | 548/427 |
| 5,268,486 | 12/1993 | Waggoner et al. | 548/427 |
| 5,486,616 | 1/1996 | Waggoner et al. | 548/217 |
| 5,627,027 | 5/1997 | Waggoner | 435/6 |
| 5,863,753 | 1/1999 | Haugland et al. | 435/34 |

OTHER PUBLICATIONS

USPATFULL 91:15050, abstract of Inagaki, US PSatent #4,994,343, 1991.
USPatFull 92:25432, abstract of Roberts, US Patent #5,100,970, 1992.
US PatFull 93:50621, abstract of Acker, US Patent #5,221,751, 1993.
USPatFull 95:1537, abstract pf Sigetoh, US Patent #5,378634, 1995.
USPatFull 96:85234, abstract of Brush, #5,556,959, 1996.
USPatFull 98:112115, abstract of Brush, #5,808,044, 1998.
Miltsov et al. "Nortricarbocyanines: New Near–Infrared pH–Indicators" Tetrahedron Letters 39 (1998) 9253–9254.
Benson et al. "Fluorescence Energy–Transfer Cyanine Heterodimers with High Affinity for Double–Stranded DNA" Analytical Biochemistry 231, 247–255 (1995).
Hung et al. "Cyanine Dyes with High Absorption Cross Section as Donor Chromophores in Energy Transfer Primers" Analytical Biochemistry 243, 15–27 (1996).
Lindsey et al. "Visible Light–Harvesting in Covalently–Linked Porphyrin–Cyanine Dyes" Tetrahedron vol. 45, No. 15, pp. 4845–4866 (1989).
Southwick et al. "Cyanine Dye Labeling Reagents–Carboxymethylindocyanine Succinimidyl Esters" Cytometry 11:418–430 (1990).
Flanagan, Jr. et al. "Functionalized Tricarbocyanine Dyes as Near–Infrared Flurescent Probes for Biomolecules" Bioconjugate Chem. 1997, 8. 751–756.
Mujumdar et al. "Cyanine Dye Labeling Reagents Containing Isothiocyanate Groups" Cytometry 10:11–19 (1989).
Ernst et al. "Cyanine Dye Labeling Reagents for Sulfhydryl Groups" Cytometry 10:3–10 (1989).
Mujumdar et al. "Cyanine Dye Labeling Reagents: Sulfoindocyanine Succinimidyl Esters" Bioconjugate Chemistry (1993) vol. 4, No. 2, pp. 105–111.
Narayanan et al. "A New Method for the Synthesis of Heptamethine Cyanine Dyes: Synthesis of New Near–Infrared Fluorescent Labels" J. Org. Chem. 1995, 60, 2391–2395.
Southwick et al. "'One Pot' Fischer Synthesis of (2,3, 3–trimethyl–3–H–indol–5–yl)–acetic acid. Derivatives as Intermediates for Fluorescent Biolabels" Oppi Briefs (1988) vol. 20, No. 3, pp. 279–284.
Reddington "New glycoconjugated cyanine dyes as fluorescent labeling reagents" 1 Perkins 7/033089 (1997).

*Primary Examiner*—D. Margaret Seaman
*Attorney, Agent, or Firm*—Gifford, Krass, Groh, Sprinkle, Anderson & Citkowski, P.C.

[57] ABSTRACT

A cyanine dye having the formula wherein $R_1$–$R_8$ are each independently selected from a group consisting of hydrogen, $C_1$–$C_6$ alkyl group, and $C_0$–$C_4$ alkyl group having a hydrophilic substituent thereon. $R_{11}$ and $R_{12}$ are chosen to include a free or protected thiol, amine or hydroxyl substituent capable of reacting with a target molecule through a nucleophilic displacement mechanism. The dye is useful in labeling a variety of target molecules. Processes are described for synthesizing suitable heterocyclic and indole derivatives as precursors for the aforementioned cyanine dyes.

15 Claims, No Drawings

CYANINE DYES AND SYNTHESIS METHODS THEREOF

FIELD OF THE INVENTION

This invention relates to the synthesis of cyanine dyes having nucleophilic reactive groups. Further, the present invention includes synthetic methods to produce free reactive thiol, amine or hydroxyl groups from protected substituents, the nucleophilic groups capable of nucleophilic addition to target molecules.

BACKGROUND OF THE INVENTION

Cyanine dyes are now recognized to have widespread application as fluorescent probes which can be conjugated to a variety of biological molecules, thus finding applications in DNA sequencing, flow cytometry and immunoassays. Cyanine dyes are characterized by strong spectral absorption bands with the absorption being tunable over a large spectral range by synthetic design.

In addition to the spectral characteristics of a cyanine dye, a practical dye is characterized by also being stable during isolation and purification, yet be reactive for covalent bonding with a target molecule under conditions which will not degrade the target molecule. Prior art cyanine dyes having reactive groups capable of covalently bonding a target molecule have all been limited in their utility either by structural stability or the reaction conditions required for coupling of the dye and target molecules.

An iodo acetyl moiety attached to a cyanine dye is capable of covalently reacting with a sulfhydryl group of a target molecule. The iodo acetyl group is limited in its utility by the sulfhydryl groups being present in only a small class of proteins. Other reactive moieties have included sulfonic acid, carboxylates, and sulfonates (for example see, Anal. Biochem. 243, 15–27: 1996; Bioconj. Chem. 4, 105–111: 1993; 8, 751–756: 1997; Cytometry 10, 3–10: 1989; 10, 11–19: 1989; U.S. Pat. No. 5,106,990; and J. Chem. Soc. Perkin Transactions 1, 143–7: 1998). Such moieties remain reactive during the course of subsequent chemical transformations and purification or are limited by the reaction conditions for bonding to a target molecule.

U.S. Pat. No. 5,627,027 is directed to a method for labeling proteins, cells, nucleic acid and DNA with a cyanine dye, as well as the reaction therebetween. The cyanine dye specified is limited in the position of a reactive group within the dye and its identity is limited to isothiocyanate, isocyanate, monochlorotriazine, dichlorotriazine, mono- or di-halogen substituted pyridine, mono- or di-halogen substituted diazine, aziridine, sulfonyl halide, acid halide, hydroxy succinimide ester, hydroxy sulfosuccinimide ester, imido ester, glyoxal and aldehyde. The method still further requires forming a covalent bond between the reactive group on the dye, and an amine or hydroxyl group on the material being labeled utilizing an electrophilic mechanism for coupling the dye and material being labeled.

U.S. Pat. No. 5,486,616 is directed to particular cyanine dye structures which are water soluble, and capable of reacting with amino, hydroxy or sulfhydryl groups through a reactive moiety. The dye structures including at least one sulfonic acid or sulfonate moiety attached directly to a benzyl portion of the dye utilizing an electrophilic mechanism for coupling the dye and material being labeled.

U.S. Pat. No. 5,268,486 discloses water soluble dyes which contain reactive moieties including isothiocyanate, isocyanate, monochlorotriazine, dichlorotriazine, mono- or di-halogen substituted pyridine, mono- or di-halogen substituted diazine, maleimide, aziridine, sulfonyl halide, acid halide, hydroxysuccinimide ester, hydroxysulfosuccinimide ester, imido ester, hydrazine, azidonitrophenyl, azide, 3-(2-pyridyl dithio)-proprionamide, glyoxal and aldehyde. These dyes are chosen to label target molecules containing amino-, hydroxy- and sulfhydryl groups.

In view of the prior art, it is apparent that there exists a need for a wider range of indole derivatives which will allow the facile synthesis of stable cyanine dyes with suitably positioned reactive groups for covalent attachment to target molecules. The cyanine dyes should allow covalent bonding to target molecules under conditions which will not degrade the target molecules. They should be stable, easily formed, purified and reactive under conditions of attachment to target molecules. This invention describes the facile synthesis of new, stable indole precursors derived from indoles. These precursors allow the facile synthesis of cyanine dyes with protected thiol, amine or hydroxyl groups. The protected groups can be deprotected to yield free thiol, amine or hydroxyl groups which can be covalently attached to target molecules via a nucleophilic mechanism.

In view of the prior art, it is apparent that there exists a need for a cyanine dye having a more generic utility. A need exists for a cyanine dye which is water soluble and contains at least one reactive moiety capable of labeling a range of substances in addition to compounds containing amino, hydroxy and sulfhydryls through covalent bonding with target molecules under conditions which will not degrade a target molecule.

Prior coupling reactions have been carried out by an electrophilic mechanism. Thus, there further exists a need for a generic class of cyanine dyes which are capable of coupling to a target molecule by a nucleophilic mechanism.

DETAILED DESCRIPTION OF THE INVENTION

The present invention relates to a class of nitrogen containing heterocyclics of the formula:

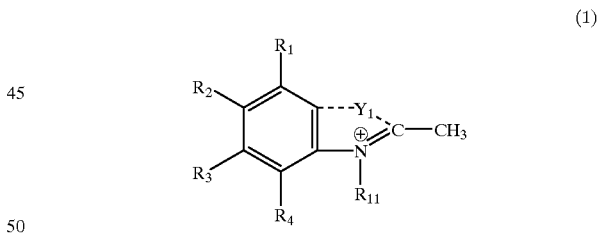

wherein $Y_1$ is selected from a group consisting of:

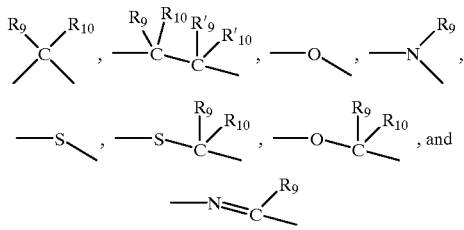

wherein $R_1$, $R_2$, $R_3$, and $R_4$ are each independently selected from a group consisting of hydrogen, $C_1$–$C_6$ alkyl group, a $C_0$–$C_4$ alkyl group having a hydrophilic substituent selected from a group consisting of sulfonate, carboxylate, hydroxyl, substituted amines and quaternary amines, optionally, at least one of $R_1$–$R_4$ is the $C_0$–$C_4$ alkyl group having the hydrophilic substituent;

wherein $R_9$, $R_9'$, $R_{10}$ and $R_{10}'$ are each independently selected from a group consisting of $C_1$–$C_{30}$ alkyl, and a heteroatom substituted $C_1$–$C_{30}$ alkyl wherein the heteroatom is O, N or S; and wherein $R_{11}$ is selected from a group consisting of

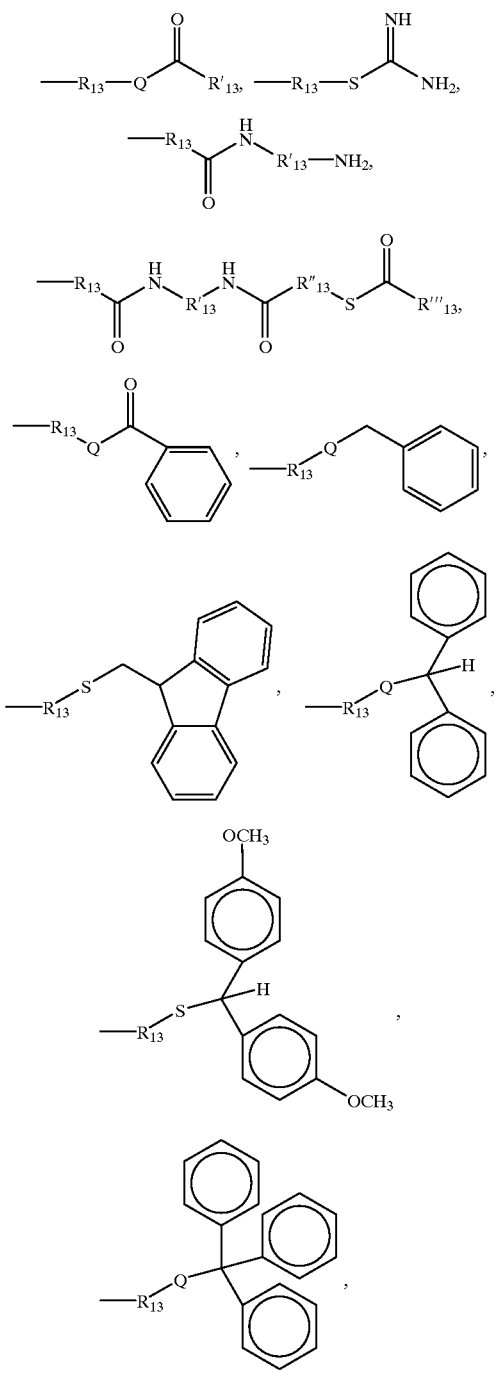

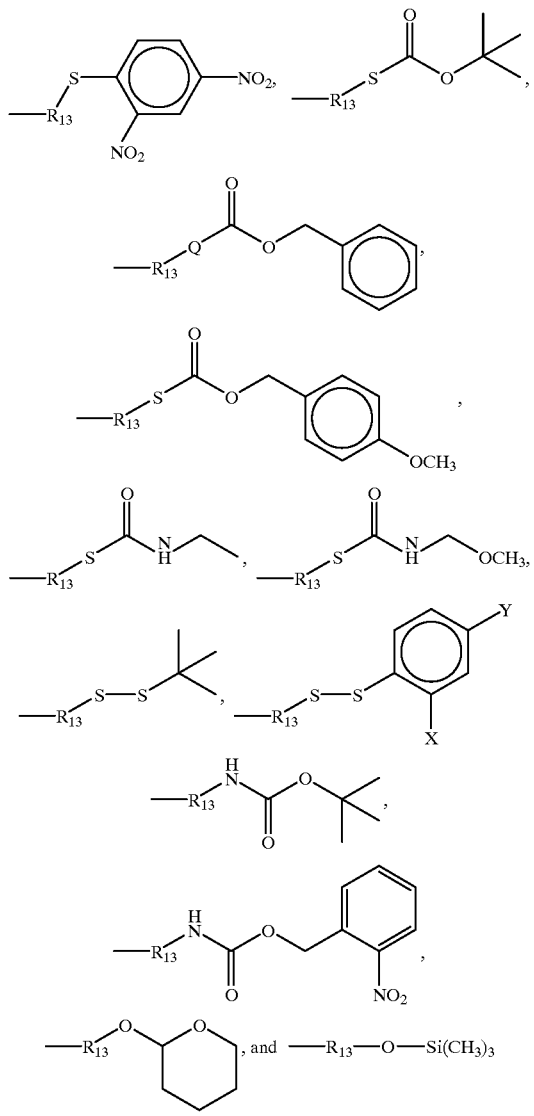

wherein $R_{13}$, $R'_{13}$, $R''_{13}$ and $R'''_{13}$ are each independently $C_1$–$C_{30}$ alkyl. Q is sulfur, nitrogen or oxygen, X is a halogen and Y is a halogen.

Prior to the present invention it has been difficult to synthesize N substituted heterocyclics and indoles in particular with hydrocarbon moieties containing protected nucleophilic groups. The present invention describes a facile reaction between bifunctional hydrocarbons containing the moiety $XR_{13}Q$ where X is chlorine, bromine or iodine, $R_{13}$ is $C_1$–$C_{30}$ alkyl and Q is sulfur, nitrogen or oxygen; and nitrogen containing heterocyclics which leads to heterocyclics having protected nucleophilic groups in the primary position on the new N-substituent or a moiety which can be converted to a protected nucleophilic group such as a thiol, amine or alcohol. The new reaction proceeds by heating a solid mixture of the precursors at elevated temperature for a short period of time. The product is purified using conventional chromatography. Alternatively the reaction proceeds by heating a suitable suspension of solid nitrogen containing heterocyclic in a suitable reagent solution. The product from the latter method can be purified using conventional methods.

Chemicals containing the indole nucleus occur widely throughout the animal and plant kingdoms and are components of chemicals found in the human body. For example, the essential amino acid tryptophan (which occurs in many peptides and bioactive proteins) contains an indole nucleus and is the biochemical precursor to serotonin which is the important neurotransmitter involved in learning, memory, depression and feeding behavior. Many naturally occurring alkaloids containing the indole nucleus such as Harmaline, Cinchera, Yohimbine, Rauwolfia and Ergot alkaloids have widely differing impacts on biological activities. Indole containing chemicals have been used in industrial applications as dye components and biochemical labeling reagents.

The new and facile chemistry described in this application enables the synthesis of many new derivatives of indole containing chemicals by providing a vehicle to add a wide variety of chemical groups to an indole nucleus allowing researchers in the life sciences access to a broader variety of biologically active molecules and labeling reagents for target molecules. For example, long chain hydrocarbons may be added to indole chemicals giving them hydrophobic qualities or alternatively linker molecules may be added that will enable the various biological activities of the indoles to be covalently attached to reporter systems or to be used as the reporter molecule in various biological systems. This chemistry can also be used to synthesize new indole derivatives having interesting and beneficial pharmaceutical properties. In research, new derivatives that act as agonists or antagonists to the various sub classes of serotonin receptors may be formed. New derivatives may also lead to new labeling reagents and alternative methods of attaching labeling reagents, such as cyanine dyes, to target molecules.

The new heterocyclic derivatives synthesized by the above methods can be converted to cyanine dyes using conventional chemistry.

These heterocyclics are operative as precursors for a generic class of cyanine dyes having a protected reactive group for nucleophilic covalent attachment to target molecules. The precursor (1) is condensed to form a fluorescent cyanine dye through a polymethine linkage.

$R_1$, $R_2$, $R_3$ and $R_4$ are optionally such that two of these adjacent R groups are fused to form a ring structure. The resulting ring structure also optionally being functionalized to modify solubility and spectral properties.

The polymethine linkage being formed by reacting two equivalents of precursor (1) in the presence of a molecule illustratively including trialkyl orthoformate, dialkyl amides, and trialkoxy alkene in the presence of a base. Preferably, the base is an organic base. The linkage reaction proceeds under ambient air in a refluxing organic solvent, although it proceeds at a slower rate without solvent reflux. The organic base illustratively includes pyridine, phenol and an alkoxide, morpholine, piperidine, t-butylamine, and triethylamine and an amine. The polymethine linkage is a conjugated system having 3, 5, 7 or more linear carbon atoms therein.

The polymethine linkage between two molecules of precursor (1) is appreciated to include linear chains, as well as also cyclo-aliphatics, substituted aryl and heterocyclic ring structures coupled to the conjugate system of the polymethine chain. For instance, a bisaldehyde is more reactive towards the precursors of the present invention than formates, amides or alkoxyalkenes and reaction does not require the presence of a base. Instead, reaction occurs in the presence of an alcohol (J. Org. Chem. 60, 2391–2395: 1995). A 1-formyl-3-(hydroxymethylene)cyclohex-1-ene derivative thus yields a heptamethine linkage. Thus, it is appreciated that modification and extension of the conjugate bonding across the chain will affect the absorption characteristics of the dye. Further, it is appreciated that additional reactive groups or solubility enhancing moieties are readily coupled to the polymethine linkage.

The resulting cyanine dye has the formula:

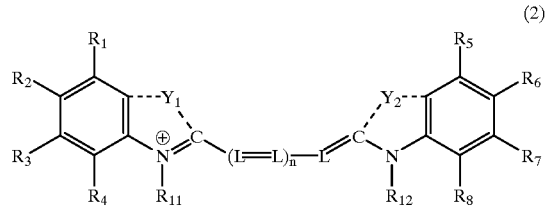

(2)

wherein $R_1$, $R_2$, $R_3$, $R_4$, $R_5$, R6, $R_7$, and $R_8$ are each independently selected from a group consisting of hydrogen, $C_1$–$C_{30}$ alkyl group, a $C_0$–$C_4$ alkyl group having a hydrophilic substituent selected from a group consisting of sulfonate, carboxylate, hydroxyl, substituted amines and quaternary amines;

wherein $Y_1$ and $Y_2$ are each independently selected from a group consisting of:

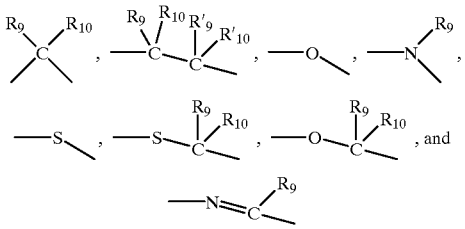

wherein $R_9$, $R'_9$, $R_{10}$, and $R'_{10}$ are each independently selected from a group consisting of $C_1$–$C_6$ alkyl, and a heteroatom substituted $C_1$–$C_6$ alkyl wherein the heteroatom is O, N or S;

wherein $R_{11}$ and $R_{12}$ are each independently selected from a group consisting of $C_1$–$C_{30}$ alkyl, phenyl substituted $C_1$–$C_{30}$, $C_1$–$C_{30}$ having a protected substituent selected from a group consisting of:

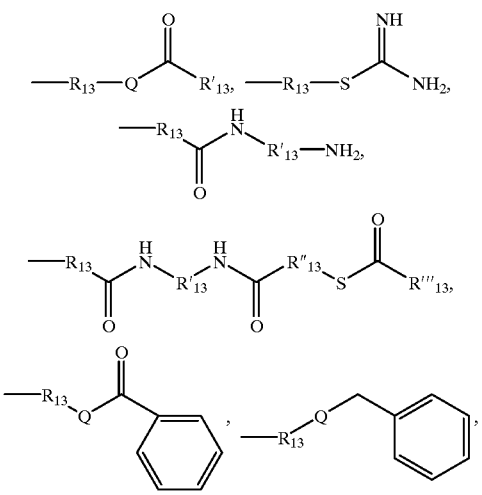

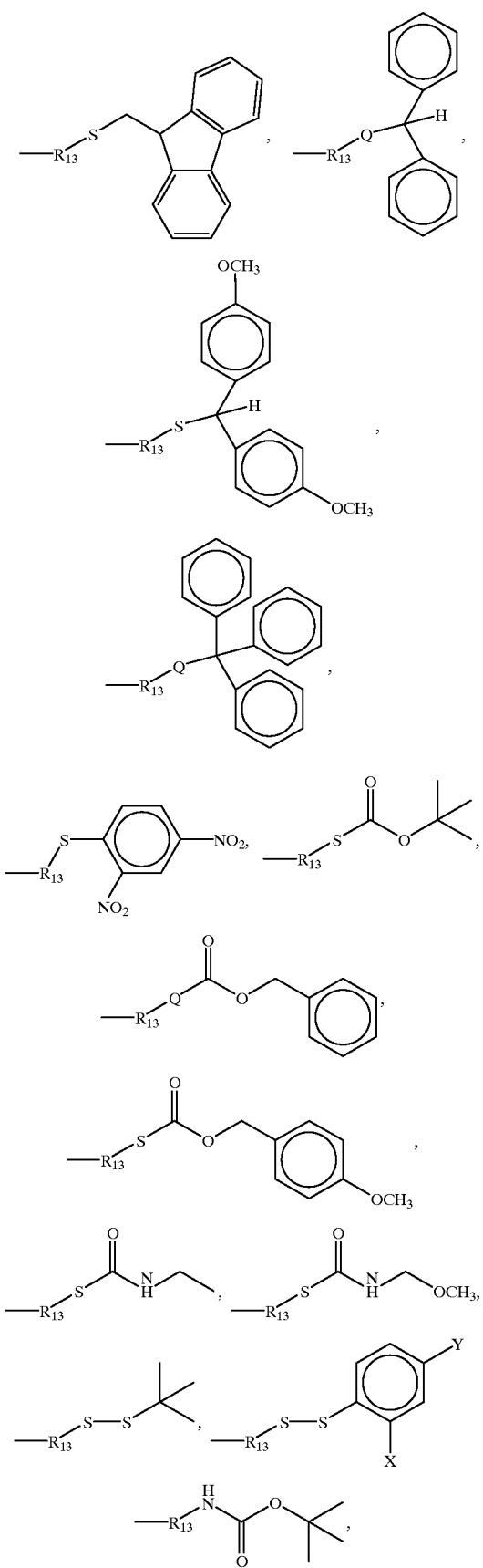

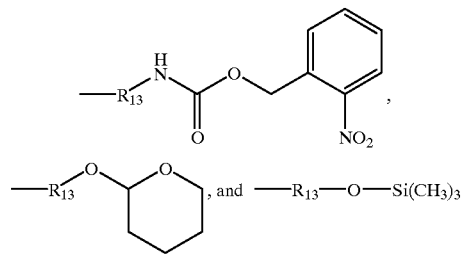

wherein $R_{13}$, $R'_{13}$, $R''_{13}$ and $R'''_{13}$ are each independently $C_1$–$C_{30}$ alkyl; Q is sulfur, nitrogen or oxygen, X is a halogen and Y is a halogen;

L is selected from a group consisting of: methine, a methine group having a substituent $C_1$–$C_6$ alkyl group and a substituted $C_1$–$C_6$ alkyl group having a phenyl, hydroxyl, sulfonyl, a halogen atom, a heteroatom substituted phenyl and a $C_1$–$C_4$ alkoxyl where n is 1, 2, 3 or greater.

$R_1$–$R_8$ are optionally such that two of these adjacent R groups are fused to form a ring structure. The resulting ring structure optionally is being functionalized to modify solubility and spectral properties.

In order to increase the water solubility of the resulting dye (2), the $R_1$, $R_2$, $R_3$, $R_4$, $R_5$, $R_6$, $R_7$, $R_8$, $R_9$, $R_9'$, $R_{10}$, $R_{10}'$, $R_{11}$ and $R_{12}$ groups are each optionally selected from well known polar and charged moieties. Preferably, each precursor molecule (1) contains at least one hydrophilic moiety in order to impart water solubility. The hydrophilic moieties illustratively include $C_0$–$C_4$ alkyl-hydroxy, -substituted amino, -quaternary amino, -sulfonate and -carboxylate. It is appreciated that hydrophobic or nonpolar precursors are useful in organic solvent systems.

A dye (2) is reactive towards a target molecule upon formation of a thiol, amine or hydroxyl moiety. The thiol, amine or hydroxyl moiety is characterized by a lone pair of electrons sterically and electronically amenable to bonding with to a reactant which is reactive towards target molecules. The reaction of a dye (2) with a deprotecting agent converts the substituent into a reactive thiol, amine or hydroxyl substituent. Deprotecting agents are well known to the art. (Theodora W. Greene and Peter G. M. Wuts, Protective Groups in Organic Synthesis, 2nd edition (1991) 277–308.) It is appreciated that an amine or hydroxyl substituent in fact optionally need not be protected, but instead are stable under synthesis conditions and are isolated as such. Thus, an amine or hydroxyl substituent operates as a reactive nucleophilic substituent without the occurrence of an intermediate deprotecting reaction.

It is appreciated that the dyes of the present invention are also amenable to isolation in deprotected form of free thiols. A free thiol containing dye of the present invention results upon reacting a dye (2) with a deprotecting agent and isolating the free thiol therefrom. The resulting free thiol, depending on its specific identity, has a shelf life of more than one month. As with other reactive thiols, free thiol cyanine dyes of the present invention are best maintained under conditions suitable to prevent the formation of disulfide linkages. These conditions illustratively include refrigeration, darkness and storage under an inert atmosphere. Alternatively, nitrogen containing heterocyclics identical to (1) except that $R_{11}$ is selected from the group consisting of $R_{14}SH$, $R_{14}NH_2$ and $R_{14}OH$ are formed directly wherein $R_{14}$ is a $C_3$–$C_{30}$ alkyl and $C_3$–$C_{30}$ alkyl having a phenyl, hydroxyl, sulfonyl, or halogen atom or a heteroatom substituted phenyl. The reaction chemistry to produce a free thiol dye precursor analog to (1) proceeds in a similar fashion to the formation of protected heterocyclics (1). For example, a cationic nitrogen-containing heterocyclic and a halogenated thiol are able to react via a metatheses reaction to create a free thiol dye precursor. The amine or hydroxyl moiety are produced by analogous type reactions. A free thiol precursor thereafter is reacted in a manner similar to precursor (1) to form a polymethine linkage therebetween. The resulting cyanine dye compound is identical to that of (2) except that $R_{11}$ and $R_{12}$ are each independently $R_{14}SH$, $R_{14}NH_2$ or $R_{14}OH$ when $R_{14}$ is a $C_3$–$C_{30}$ alkyl or $C_3$–$C_{30}$ alkyl having a phenyl, hydroxyl, sulfonyl, or halogen atom or a heteroatom substituted phenyl.

A commercial package of the present invention includes a compound of Formula (1) with instructions and optionally reagents for converting the precursor (1) to a dye compound (2) and further instructions for the use of the dye compound (2) as a dye or hapten. It is appreciated that a free thiol, amine or hydroxyl analog of a compound (1) is also operative herein. Alternatively, a commercial package includes a compound (2) as an active ingredient together with instructions for the use thereof as a dye or hapten in labeling a target molecule. It is also appreciated that a free thiol, amine or hydroxyl analog of a compound (2) is also operative herein.

The addition of a reactive form of a dye (2) to a target molecule proceeds under conventional nucleophilic reaction conditions. The solvent for the nucleophilic reaction being dictated by the identity of the target molecule. Since many target molecules of interest are of a biological nature, water is often the nucleophilic reaction solvent.

A target molecule which is coupled with a dye of the present invention illustratively includes organic molecules, polymers, silaceous materials, natural and synthetic: lipid vesicles, amino acids, peptide nucleic acids, peptides, nucleic acids, nucleotides, nucleosides, DNA, RNA, proteins, carbohydrates, oligosaccharides, polysaccharides, antibodies, cellular receptors, antigens, haptens, lectins, avidins, streptavidins, lymphokines, hormones, metabolites, toxins, virions, bacteria, fungal components, esinophils, eukaryotic cells, and derivatives thereof.

A dye (2) of the present invention in which neither $R_{11}$ or $R_{12}$ is $C_1$–$C_{30}$ having a heteroatom containing substituent finds utility as a physi-sorbed, fluorescent dye. Alternatively, a dye of the present invention lacking a heteroatom within $R_{11}$ or $R_{12}$ is coupled to a target molecule through a hydrophilic moiety of $R_1$–$R_8$ or a pendant reactive moiety extending from the polymethine linkage.

In order to more fully demonstrate the advantages arising from the present invention, the following examples are set forth. It is to be understood that the following is by way of example only and not intended as a limitation on the scope of the invention.

EXAMPLE 1

Dye precursor 1-[3-S-Acetylthiopropyl]-2,3,3-trimethyl-5-sulfo-3H-indolium, inner salt (5).

To a 250 mL round bottom flask with magnetic stir bar is added 2,3,3-trimethyl-5-sulfo-3H-indolium, potassium salt (3) (7.21 mmol) and 3-bromo-1-thioacetylpropane (4) (25.88 mmol). The mixture is stirred and heated at 165° C. for 20 min. The residue is cooled to 20° C. and washed with diethyl ether. The solid is purified by Reversed Phase Chromatography to give 1-[3-S-Acetylthio-propyl]-2,3,3-trimethyl-5-sulfo-3H-indolium, inner salt (5) as a solid.

EXAMPLE 2

Dye precursor 1-[3-S-Acetylthiopropyl]-2,3,3-trimethyl-5-hydroxyl-6-benzo-3H-indolium, inner salt (7).

The procedure of Example 1 is repeated except 2,3,3-trimethyl-5-hydroxyl-6-benz-indolium, potassium salt (6) is substituted for (3). A solid product 1-[3-S-Acetylthiopropyl]-2,3,3-trimethyl-5-hydroxyl-6-benzo-3H-indolium, inner salt (7) is isolated.

EXAMPLE 3

Dye precursor 1-[4-S-benzoylbutyl]-3-methyl-4-carboxyl benzoxizolium, inner salt (10).

The procedure of Example 1 is repeated except 3-methyl-4-carboxyl benzoxizolium, sodium salt (8) is substituted for (3) and 4-bromo-1-S-benzoylbutane (9) is substituted for (4). A solid product 1-[4-S-benzoylbutyl]-3-methyl-4-carboxyl benzoxizolium, inner salt (10) is isolated.

EXAMPLE 4

Dye precursor 1-[3-S-t-butylpropyl]-3-methyl-5-sulfo-benzoimidazolium, inner salt (13).

The procedure of Example 1 is repeated except 3-methyl-5-sulfo-benzoimidazolium (11) and 3-bromo-1-S-t-butyl propane (12) is substituted for (4). A solid product 1-[3-S-t-butylpropyl]-3-methyl-5-sulfo-benzoimidazolium, inner salt (13) is isolated.

EXAMPLE 5

Cyanine-3 Dyes Derived from (5).

A solution of (5) (2.68 mmol) and 1-ethyl-2,3,3-trimethyl-5-sulfo-3H-indolium, inner salt (14) (2.68 mmol) is heated to reflux in pyridine (70 mL) and triethyl orthoformate (24.0 mmol) is added via syringe over 1 hour in four equal portions. The suspension is then heated to reflux for an additional 3 hours and cooled to room temperature. The solvents are removed under reduced pressure and the solid is azeotroped two times with methanol. The solid is purified by Reversed Phase Chromatography and the isolated products are passed over an AG50W-X4, 200–400 mesh K+ form, column to give 1-[3-S-acetylthiopropyl]-2-[3-[1-ethyl-1,3-dihydro-3,3-dimethyl-5-sulfo-2H-indol-2-ylidene]-1-propenyl]-3,3-dimethyl-5-sulfo-3H-indolium, potassium salt (15), 1-[3-S-Acetylthiopropyl]-2-[3-[1-[3-S-acetylthiopropyl]-1,3-dihydro-3,3-dimethyl-5-sulfo-2H-indol-2-ylidene]-1-propenyl]-3,3-dimethyl-5-sulfo-3H-indolium, potassium salt (16), and 1-ethyl-2-[3-[1-ethyl-1,3-dihydro-3,3-dimethyl-5-sulfo-2H-indol-2-ylidene]-1-propenyl]-3,3-dimethyl-5-sulfo-3H-indolium, potassium salt (17) as solids.

EXAMPLES 6–10

Cyanine-3 Dyes Derived from (7), (10) and (13).

The procedure of Example 5 is repeated with (7), (10) and (13) substituted for (5) and the 1-ethyl-analogs of (7), (10) and (13) substituted for (14). The resulting solid compounds which are isolated in purified form are summarized in Table 1.

EXAMPLE 11

Cyanine-5 Dyes Derived from (5).

A solution of (5) (1.60 mmol), (14) (1.60 mmol) and potassium acetate (3.56 mmol) in methanol (50 mL) is heated to reflux and 1,3,3-trimethoxypropene (21.0 mmol) is added via syringe over 1 hour in four equal portions. The suspension is then heated to reflux for an additional 3 hours and cooled to room temperature. The methanol is removed under reduced pressure and the solid is purified by Reversed Phase Chromatography to give 1-[3-S-Acetylthiopropyl]-2-[5-[1-ethyl-1,3-dihydro-3,3-dimethyl-5-sulfo-2H-indol-2-ylidene]-1,3-pentadienyl]-3,3-dimethyl-5-sulfo-3H-indolium, potassium salt (29), 1-[3-S-Acetylthiopropyl]-2-[3-[1-[5-S-acetylthiopropyl]-1,3-dihydro-3,3-dimethyl-5-sulfo-2H-indol-2-ylidene]-1,3-pentadienyl]-3,3-dimethyl-5-sulfo-3H-indolium, potassium salt (30) and 1-ethyl-2-[5-[1-ethyl-1,3-dihydro-3,3-dimethyl-5-sulfo-2H-indol-2-ylidene]-1,3-pentadienyl]-3,3-dimethyl-5-sulfo-3H-indolium, potassium salt (31) as solids.

EXAMPLE 12

Dye Precursor S-(3-Iodopropyl)isothiourea (32).

Thiourea (14 mmol) is added to a solution of 1,3-diiodopropane (340 mmol) in anhydrous methanol (300 mL) and stirred under an atmosphere of nitrogen at 60° C. for 4 hours. The solution is cooled to 4° C. overnight during which time excess 1,3-diiodopropane separates to the bottom of the flask as a colorless oil. The excess 1,3-diiodopropane is removed by pipette and the remaining methanol solution is evaporated in vacuo and the residue is suspended in dichloromethane, filtered, and washed with additional dichloromethane to give S-(3-Iodopropyl)isothiourea (32) as a powder.

EXAMPLE 13

Dye Precursor 1-[3-Isothiouronylpropyl]-2,3,3-trimethyl-5-sulfo-3H-indolium, inner salt (33).

A solution of (32) (0.36 mmol) and 2,3,3-trimethylindolium-5-sulfonate, potassium salt (3) (0.46 mmol) are placed in a flask and heated to 148° C. with stirring for 15 minutes under an atmosphere of nitrogen. The reaction mixture is cooled to room temperature and the residue is crystallized from methanol to give 1-[3-isothiouronylpropyl]-2,3,3-trimethyl-5-sulfo-3H-indolium, inner salt (33) as a powder.

EXAMPLE 14

Cyanine-3 Dyes Derived from (33).

A solution of (33) (0.022 mmol) and 1-ethyl-2,3,3-trimethyl-5-sulfo-3H-indolium, inner salt (14) (0.022 mmol) are dissolved in N,N-dimethylformamide containing 50 uL of triethylamine and the mixture is heated to 60° C. as triethylorthoformate (4×10 uL, 4×0.06 mmol) is added in four portions over 3 hours. The solution is heated at 60° C. for an additional hour, cooled to room temperature, washed 3 times with diethyl ether, and the resulting precipitate is purified by reverse phase HPLC to give isolated 1-[3-Isothiouronylpropyl]-2-[3-[1-ethyl-1,3-dihydro-3,3-dimethyl-5-sulfo-2H-indol-2-ylidene]-1-propenyl]-3,3-dimethyl-5-sulfo-3H-indolium, potassium salt (34), 1-[3-Isothiouronylpropyl]-2-[3-[1-[3-isothiouronylpropyl]-1,3-dihydro-3,3-dimethyl-5-sulfo-2H-indol-2-ylidene]-1-propenyl]-3,3-dimethyl-5-sulfo-3H-indolium, potassium salt (35) and 1-ethyl-2-[3-[1-ethyl-1,3-dihydro-3,3-dimethyl-5-sulfo-2H-indol-2-ylidene]-1-propenyl]-3,3-dimethyl-5-sulfo-3H-indolium, potassium salt (17) as solids.

EXAMPLE 15

Bonding of Dye (15) to a Target Nucleotide Derivative.

To a 2 mL vial with a stir bar is added (15) (1.58 μmol), 5-[3-[3-[2,5-dihydro-2,5-dioxo-1H-pyrrole]propanamido]-1-propynyl]-2'-deoxycytidine triphosphate (36) (5.0 μmol) in 50 mM sodium dihydrogenphosphate pH 7.0–7.5 (250 μL). To the stirred solution is added 1M hydroxylamine pH 7.0–7.5 (250 μL) and the resulting solution is stirred at room temperature for 1 hour. The reaction mixture is purified to give 5-[3-[3-[3-[1-[3-thiopropyl]-2-[3-[1-ethyl-1,3-dihydro-3,3-dimethyl-5-sulfo-2H-indol-2-ylidene]-1-propenyl]-3,3-dimethyl-5-sulfo-3H-indolium]-2,5-pyrrolidindione]propanamido]-1-propynyl]-2'-deoxycytidine triphosphate (37).

EXAMPLE 16

Bonding of Dye (28) to a Target Nucleotide Derivative.

The procedure of Example 15 is repeated with (28) substituted for (15). The reaction mixture is purified to give 5-[3-[3-[3-[1-[3-thiopropyl]-2-[3-[1-ethyl-3-methyl-5-sulfo-benz-imidazol-2-ylidene]-1-propenyl]-3,3dimethyl-5-hydroxyl-6-benz-indolium]-2,5-pyrrolidindione]propanamido]-1-propynyl]2'-deoxycytidine triphosphate (38).

EXAMPLE 17

Bonding of Dye (29) to a Target Nucleotide Derivative.

The procedure of Example 15 is repeated with (29) substituted for (15). The reaction mixture is purified to give 5-[3-[3-[3-1-[3-thiopropyl]-2-[5-[1ethyl-1,3-dihydro-3,3-dimethyl-5-sulfo-2H-indol-2-ylidene]-1,3-pentadienyl]-3,3-dimethyl-5-sulfo-3H-indolium]-2,5-pyrrolidindione]propanamido]-1-propynyl]-2'-deoxycytidine triphosphate (39).

EXAMPLE 18

Dye Precursor 1-[3-Isothiouronylpropyl]-2,3,3-trimethyl-3H-indolium Iodide (41).

To a 50 mL round bottom flask is added 2,3,3-trimethylindolenine (14.4 mmol) and 1,3-diiodopropane (72.7 mmol) and the mixture is stirred at 60° C. under an atmosphere of nitrogen for 16 hours. The resulting solid is recrystallized from ethanol to give 1-[3-iodopropyl]-2,3,3-trimethyl-3H-indolium iodide (40) as crystals.

To a 100 mL round bottom flask is added (40) (4.38 mmol), thiourea (4.5 mmol), and methanol (30 mL). The solution is stirred at 60° C. for 5 hours, evaporated in vacuo, the residue is dissolved in water (20 mL) and washed with dichloromethane (3×6 mL) and cooled to 4° C. overnight, and the resulting crystals are filtered and washed with acetone to give 1-[3-isothiouronylpropyl]-2,3,3-trimethyl-3H-indolium iodide (41).

EXAMPLE 19

Cyanine-3 Dyes Derived from (41).

To a 25 mL round bottom flask is added (41) (1.0 mmol), (14) (1.5 mmol), and pyridine (10 mL). The solution is heated to reflux and triethyl orthoformate (4×166 uL, 4×1.0 mmol) is added in four portions over one hour. The solution is heated at reflux for an additional hour, cooled to room temperature, the evaporated in vacuo, and the residue is washed with ethyl ether (3×25 mL), and purified by C18 reverse phase chromatography to give isolated 1-[3-isothiouronylpropyl]-2-[3-[1-ethyl-1,3-dihydro-3,3-dimethyl-5-sulfo-2H-indol-2-ylidene]-1-propenyl]-3,3-dimethyl-3H-indolium, inner salt (42), 1-[3-isothiouronylpropyl]-2-[3-[1-[3-isothiouronylpropyl]-1,3-dihydro-3,3-dimethyl-2H-indol-2-ylidene]-1-propenyl]-3,3-dimethyl-3H-indolium iodide (43) and 1-ethyl-2-[3-[1-ethyl-1,3-dihydro-3,3-dimethyl-5-sulfo-2H-indol-2-ylidene]-1-propenyl]-3,3-dimethyl-5-sulfo-3H-indolium, potassium salt (17) as solids.

EXAMPLE 20

Cyanine-5 Dyes Derived from (41).

A solution of (41) (0.28 mmol) and (14) (0.28 mmol) and potassium acetate (0.28 mmol) in methanol (2 mL) is heated to reflux and 1,3,3-trimethoxypropene (160 uL, 1.17 mmol) is added via syringe over 2 hour in four equal portions. A suspension is then heated to reflux for an additional 3 hours and cooled to room temperature. The methanol is removed under reduced pressure and the solid is purified by C18 Reversed Phase Chromatography to give 1-[3-isothiouronylpropyl]-2-[5-[1-ethyl-1,3-dihydro-3,3-dimethyl-5-sulfo-2H-indol-2-ylidene]-1,3-pentadienyl]-3,3-dimethyl-3H-indolium, inner salt (44), the related di-isothiouronyl-propyl and diethyl inner salts as solids.

EXAMPLE 21

Bonding of Dye (42) to a Target Nucleotide Derivative.

To a 2 mL vial with a stir bar is added 1-[3-isothiouronylpropyl]-2-[3-[1-ethyl-1,3-dihydro-3,3-dimethyl-5-sulfo-2H-indol-2-ylidene]-1-propenyl]-3,3-dimethyl-3H-indolium, inner salt (42) (8 μmol) in 0.1 M potassium hydroxide (1.0 mL). The solution is stirred at room temperature for 1 hour to form the free thiol of (42). Thereafter, (36) (15 μmol) is added to the thiol in aqueous solution. The reaction mixture is purified to give 5-[3-[3-[3-[1-[3-thiopropyl]-2-[3-[1-ethyl-1,3-dihydro-3,3-dimethyl-5-sulfo-2H-indol-2-ylidene]-1-propenyl]-3,3-dimethyl-3H-indolium]-2,5-pyrrolidindione]propanamido]-1-propynyl]-2'-deoxycytidine triphosphate (45).

EXAMPLE 22

Bonding of Dye (44) to a Target Nucleotide Derivative.

The procedure of Example 21 is repeated with (44) substituted for (42). The reaction mixture is purified to give 5-[3-[3-[3-[1-[3-thiopropyl]-2-[5-[1-ethyl-1,3-dihydro-3,3-dimethyl-5-sulfo-2H-indol-2-ylidene]-1,3-pentadienyl]-3,3-dimethyl-3H-indolium]-2,5-pyrrolidindione]propanamido]-1-propynyl]-2'-deoxycytidine triphosphate (46).

EXAMPLE 23

Bonding of dye (15) to a Target Nucleotide Derivative.

To a 5 mL vial with a stir bar is added (15) (19 μmol), 5-[3-[iodoacetamido]-1-propynyl]-2'-deoxycytidine triphosphate (47) (30.0 μmol) in 50 mM sodium dihydrogenphosphate pH 7.0–7.5 (250 μL). To the stirred solution 1M hydroxylamine pH 7.0–7.5 (250 μL) is added. The resulting solution is stirred at room temperature for 4 hours to react the free thiol of (15) with (47). The reaction mixture is purified to give 5-[3-[1-[3-thiopropyl]-2-[3-[1-ethyl-1,3-dihydro-3,3-dimethyl-5-sulfo-2H-indol-2-ylidene]-1-propenyl]-3,3-dimethyl-5-sulfo-3H-indolium]acetamido-1-propynyl]-2'-deoxycytidine triphosphate (48).

EXAMPLE 24

Bonding of Dye (29) to a Target Nucleotide Derivative.

The procedure of Example 23 is repeated with (29) substituted for (15). The reaction mixture is purified to give 5-[3-[1-[thiopropyl]-2-[5-[1-ethyl-1,3-dihydro-3,3-dimethyl-5-sulfo-2H-indol-2-ylidene]-1,3-pentadienyl]-3,3-dimethyl-5-sulfo-3H-indolium]acetamido-1-propynyl]-2'-deoxycytidine triphosphate (49).

EXAMPLE 25

Dye Precursor 1-[N-[-3-(tert-butyloxycarbonylamino) propyl]hexanamide]-2,3,3-trimethyl-5-sulfo-3H-indolium, Inner Salt (51).

To a 100 mL round bottom flask with a stir bar is added 1-[N-[5-carboxypentyl]-2,3,3-trimethyl-5-sulfo-3H-indolium, inner salt (50) (1.70 mmol) and 40 mL of N,N-dimethylformamide. The mixture is heated at 50° C. until a homogeneous solution is obtained. To this solution is added 1,3-dicyclohexylcarbodiimide (2.30 mmol), N-hydroxysuccinimide (2.34 mmol) and t-butyl N-(3-aminopropyl)carbamate (2.29 mmol). The reaction mixture is heated at 50° C. for 30 min and then room temperature 16 hours. The reaction mixture is filtered, the solvents are removed under reduced pressure and the solid is azeotroped two times with methanol. The solid is purified by Reversed Phase Chromatography to give 1-[N-[-3-(tert-butyloxycarbonylamino)propyl]hexanamide]-2,3,3-trimethyl-5-sulfo-3H-indolium, inner salt (51) as a solid.

EXAMPLE 26

Cyanine-3 Dyes Derived from (51).

A solution of (51) (0.291 mmol) and (14) (0.281 mmol) is heated to reflux in pyridine (30 mL) and triethyl orthoformate (2.4 mmol) is added via syringe over 1 hour in four equal portions. The suspension is then heated to reflux for an additional 4 hours and cooled to room temperature. The solvents are removed under reduced pressure and the solid is azeotroped two times with methanol. The purple solid is purified by Reversed Phase Chromatography and the isolated products are passed over an AG50W-X4, 200–400 mesh K+ form, column to give 1-[N-[3-(tert-butyloxycarbonylamino)-propyl]hexanamide]-2-[3-[1-ethyl-1,3-dihydro-3,3-dimethyl-5-sulfo-2H-indol-2-ylidene]-1-propenyl]-3,3-dimethyl-5-sulfo-3H-indolium, potassium salt (52), 1-[N-[3-(tert-butyloxycarbonyl-amino)propyl]hexanamide]-2-[3-[1-[N-[3-(tert-butyloxycarbonylamino)-propyl]hexanamide]-1,3-dihydro-3,3-dimethyl-5-sulfo-2H-indol-2-ylidene]-1-propenyl]-3,3-dimethyl-5-sulfo-3H-indolium, potassium salt (53) and the related diethyl salt as solids.

EXAMPLE 27

Cyanine-5 Dyes Derived from (51).

A solution of (51) (0.291 mmol) and (14) (0.292 mmol) and potassium acetate (78 mg, 0.79 mmol) in methanol (15 mL) is heated to reflux and 1,3,3-trimethoxypropene (0.5 mL, 3.64 mmol) is added via syringe over 1 hour in four equal portions. The suspension is then heated to reflux for an additional 3 hours and cooled to room temperature. The methanol is removed under reduced pressure and the solid is purified by Reversed Phase Chromatography to give 1-[N-[3-(tert-butyloxycarbonylamino)propyl]-hexanamide]-2-[5-[1-ethyl-1,3-dihydro-3,3-dimethyl-5-sulfo-2H-indol-2-ylidene]-1,3-pentadienyl]-3,3-dimethyl-5-sulfo-3H-indolium, potassium salt (54), 1-[N-[3-(tert-butyloxycarbonyl-amino)propyl]hexanamide]-2-[5-[1-[N-[3-(tert-butyloxycarbonylamino)propyl]-hexanamide]-1,3-dihydro-3,3-dimethyl-5-sulfo-2H-indol-2-ylidene]-1,3-pentadienyl]-3,3-dimethyl-5-sulfo-3H-indolium, potassium salt (55) and the related diethyl salt as solids.

EXAMPLE 28

Bonding of Dye (44) to a Target Nucleotide Derivative.

To a 2 mL vial with a stir bar is added (44) (17 μmol) and 1 M potassium phosphate (4.0 mL) and methanol (2 mL) and the resulting solution is stirred at room temperature for 1 hour to give 1-[3-thiopropyl]-2-[5-[1-ethyl-1,3-dihydro-3,3-dimethyl-5-sulfo-2H-indol-2-ylidene]-1,3-pentadienyl]-3,3-dimethyl-3H-indolium, inner salt (56). To this solution is added (36) (34 μmol) and the reaction mixture is stirred for 1 hour and then purified to give 5-[3-[3-[3-[1-[3-thiopropyl]-2-[5-[1-ethyl-1,3-dihydro-3,3-dimethyl-5-sulfo-2H-indol-2-ylidene]-1,3-pentadienyl]-3,3-dimethyl-3H-indolium]-2,5-pyrrolidindione]propanamido]-1-propynyl]-2'-deoxycytidine triphosphate (46).

EXAMPLE 29

Bonding Dye (15) with Streptavidin.

Streptavidin (15 mg) is dissolved in 1 mL 0.1M sodium phosphate buffer, pH 7.0. Sulfosuccinimidyl 4-[N-maleimidomethyl]cyclohexane-1-carboxylate (9 mg) in 0.2 mL dimethylsulfoxide is added to the streptavidin solution at room temperature, mixed for 1 hour and purified by gel filtration chromatography to give maleimide derivatized streptavidin. To a 1.5 mL solution of maleimide derivatized streptavidin (3.5 mg) in 0.1M sodium phosphate, 5 mM EDTA buffer, pH 6.0, 1 mg of Cyanine 3 Dye (15) is added followed by 0.15 mL of 1M hydroxylamine pH 7.0. The solution is mixed at room temperature for 1 hour and then 20 μL of 0.1M N-ethylmaleimide is added and the mixture is stored at 4° C. for 16 hours. The mixture is purified by gel filtration chromatography to give streptavidin modified with Cyanine 3 Dye (15).

EXAMPLE 30

Bonding Dye 16 with Streptavidin.

Streptavidin (15 mg) is dissolved in 1 mL 0.1M sodium phosphate buffer, pH 7.0. Sulfosuccinimidyl 4-[N-maleimidomethyl]cyclohexane-1-carboxylate (9 mg) in 0.2 mL dimethylsulfoxide is added to the streptavidin solution at room temperature, mixed for 1 hour and purified by gel filtration chromatography to give maleimide derivatized streptavidin. To a 1.5 mL solution of maleimide derivatized streptavidin (3.5 mg) in 0.1M sodium phosphate, 5 mM EDTA buffer, pH 6.0, 1 mg of Cyanine 3 Dye (16) is added followed by 0.15 mL of 1M hydroxylamine pH 7.0. The solution is mixed at room temperature for 1 hour and then 20 μL of 0.1M N-ethylmaleimide is added and the mixture is stored at 4° C. for 16 hours. The mixture is purified by gel filtration chromatography to give streptavidin modified with Cyanine 3 Dye (16).

EXAMPLE 31

Bonding of dye (15) with Neurotensin on Resin.

Fmoc-Neurotensin on Resin (Wang polymer) 100 mg (substitution 0.6 mmol/g) is swelled in dimethy formamide (DMF) for 30 minutes where Fmoc has the structure:

(57)

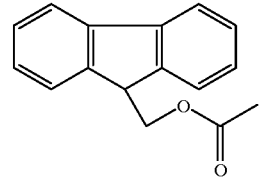

Fmoc is removed by reaction with 25% Piperidine/DMF (about 20 ml×3 min, wash with DMF, and 20 ml×20 min). Resin is washed with DMF 7×20 ml (1 min each washing step). 25 mg of (N-[gamma-malemidobutyloxy]succinimide ester (Sulfo-GMBS) in DMF (15 ml) is added and mixed with resin 24 hours. After reaction the resin is washed 7×20 ml of DMF. Cyanine (15) (10 mg) solution in DMF/ methanol (15 ml) is added along with 5 ml 1 M solution of hydroxylamine in water. Reaction is performed overnight. After washing with DMF (7×20 ml) and methanol (3×30 ml) resin is dried. Labeled peptide is cleaved from resin with Reagent K (92.5% TFA/2.5% EDT/2.5% water/2.5% TIS) 10 ml for 2 hours. Crude peptide is precipitated with cold diethyl ether and centrifuged. Precipitate is dissolved in 50% Acetonitrile/water and lyophilized.

EXAMPLE 32

Bonding of Dye (15) with Galanin on Resin.

Fmoc-Galinin on Resin is swelled as in Example 31. Orthogonal protection on Lys 25 ((4,4-dimethyl-2, 6dioxocyclohex-1-ylidene) ethyl-Dde) is removed by reaction with 2% hydrazine hydrate (2×20 ml, 2 min). Resin is washed 6 times with DMF (20 ml). 25 mg of Sulfo-GMBS in DMF (15 ml) is added and mixed with resin for 24 hours. After reaction the resin was washed 7×20 ml of DMF, (15) (10 mg) solution in DMF/MeOH (15 ml) is added along with 5 ml 1 M solution of hydroxylamine in water. Reaction is performed overnight. Labeled galanin is purified and isolated as per Example 32.

EXAMPLE 33

Bonding of Dye (29) with a Native Peptide—bradykinin.

Bradykinin (3 mg) dissolved in 1 ml of 50 mM sodium dihydrogen phosphate pH 7.5, and added sulfoGMBS (3.4 mg), mixed for 2 hours in room temperature. To the reaction mixture is added 1 ml of solution (5.8 mg) of (29) in sodium dihydrogen phosphate pH 7.5 and 0.5 ml 1 M hydroxylamine (pH 7), and mixed overnight. Labeled peptide is lyophilized.

EXAMPLE 34

Bonding of Dye (29) with Liposomes.

The procedure of Example 33 is repeated with the substitution of liposomes as per Example 1 of U.S. Pat. No. 4,089,801 for bradykinin, where the liposome includes lecithin and amyloglucoside therein. A labeled liposome is purified therefrom.

EXAMPLE 35

Bonding of 1-[3-N-acetylaminopropyl]-2-[5-1-[ethyl-1,3 dihydro-3,3-dimethyl-5-sulfo-2H-indol-2-ylidene]-1,3-pentadienyl]-3,3-dimethyl-5-sulfo-3H-indolium, Potassium Salt (58) to a Target Nucleotide Derivative.

The dye (58) is prepared as per Examples 1 and 11 using the amine analog to the dye precursor (5). The dye (58) is combined with (36) as per Example 28 to yield the amine analog to (46).

Those skilled in the art will appreciate from the foregoing description and examples that the broad teaching of the present invention can be implemented in a variety of forms. Therefore, while this invention has been described in connection with particular examples thereof, the true scope of the invention should not be so limited since other modifications will become apparent to one skilled in the art upon review of the specification and the following claims.

All patents and other publications cited herein are expressly incorporated by reference to the same extent as if each individual publication were specifically and individually indicated to be incorporated by reference.

wherein $R_1$, $R_2$, $R_3$, and $R_4$ are each independently selected from a group consisting of hydrogen, $C_1$–$C_6$ alkyl group, a $C_0$–$C_4$ alkyl group having a hydrophilic substituent selected from a group consisting of sulfonyl, carboxyl, hydroxyl, substituted amines and quaternary amines;

wherein $R_9$, $R_9{'}$, $R_{10}$ and $R_{10}{'}$ are each independently selected from a group consisting of $C_1$–$C_{30}$ alkyl, and a heteroatom substituted $C_1$–$C_{30}$ alkyl wherein the heteroatom is O, N or S; and

TABLE 1

Cyanine-3 dyes derived from precursors (7), (10), (13) and the 1-ethyl analogs thereof in terms of dye formula (2)

| Example | Compound # | $R_1$ | $R_2$ | $R_3$ | $R_4$ | $R_5$ | $R_6$ | $R_7$ | $R_8$ | $Y_1$ | $Y_2$ | $R_{11}$ | $R_{12}$ |
|---|---|---|---|---|---|---|---|---|---|---|---|---|---|
| 6 | (18) | H | OH | —$C_4H_4$— | | H | OH | —$C_4H_4$— | —$C(C_2H_5)_2$— | —$C(C_2H_5)_2$— | $C_3H_6SC(O)CH_3$ | $C_2H_5$ |
| (7) + 1-Et (7) | (19) | H | OH | —$C_4H_4$— | | H | OH | —$C_4H_4$— | —$C(C_2H_5)_2$— | —$C(C_2H_5)_2$— | $C_3H_6SC(O)CH_3$ | $C_3H_6SC(O)CH_3$ |
| | (20) | H | OH | —$C_4H_4$— | | H | OH | —$C_4H_4$— | —$C(C_2H_5)_2$— | —$C(C_2H_5)_2$— | $C_2H_5$ | $C_2H_5$ |
| 7 | (21) | COO$^-$ | H | H | H | COO$^-$ | H | H | H | —O— | —O— | $C_4H_8SC(O)C_6H_5$ | $C_2H_5$ |
| 10 + 1-Et (10) | (22) | COO$^-$ | H | H | H | COO$^-$ | H | H | H | —O— | —O— | $C_4H_8SC(O)C_6H_5$ | $C_4H_8SC(O)C$ |
| | (23) | COO$^-$ | H | H | H | COO$^-$ | H | H | H | —O— | —O— | $C_2H_5$ | $C_2H_5$ |
| 8 | (24) | H | $SO_3^-$ | H | H | H | $SO_3^-$ | H | H | —$N(CH_3)$— | —$N(CH_3)$— | $C_4H_8SC(CH_3)_3$ | $C_2H_5$ |
| 13 + 1-Et (10) | (25) | H | $SO_3^-$ | H | H | H | $SO_3^-$ | H | H | —$N(CH_3)$— | —$N(CH_3)$— | $C_4H_8SC(CH_3)_3$ | $C_4H_8SC(CH_3)_3$ |
| | (26) | H | $SO_3^-$ | H | H | H | $SO_3^-$ | H | H | —$N(CH_3)$— | —$N(CH_3)$— | $C_2H_5$ | $C_2H_5$ |
| 9 7 + 1-Et (10) | (19) (23) (27) | H | OH | —$C_4H_4$— | | COO$^-$ | H | H | H | —$C(C_2H_5)_2$— | —O— | $C_3H_6SC(O)CH_3$ | $C_2H_5$ |
| 10 (7) + 1-Et (13) | (19) (26) (28) | H | OH | —$C_4H_4$— | | H | $SO_3^-$ | H | H | —$C(C_2H_5)_2$— | —$N(CH_3)$— | $C_3H_6SC(O)CH_3$ | $C_2H_5$ |

*Note: In Examples 6–10 L is CH and n is 1.

What is claimed is:

1. A compound of the formula:

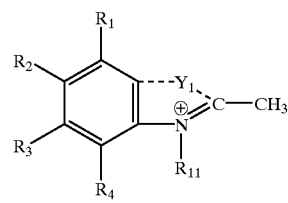

wherein $Y_1$ is selected from a group consisting of:

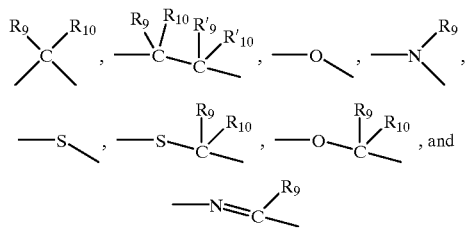

wherein $R_{11}$ is selected from a group consisting of:

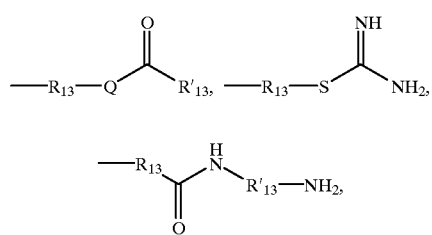

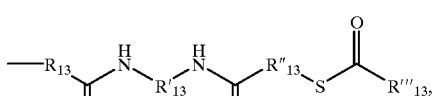

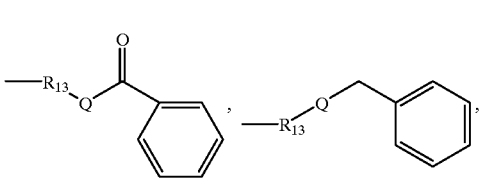

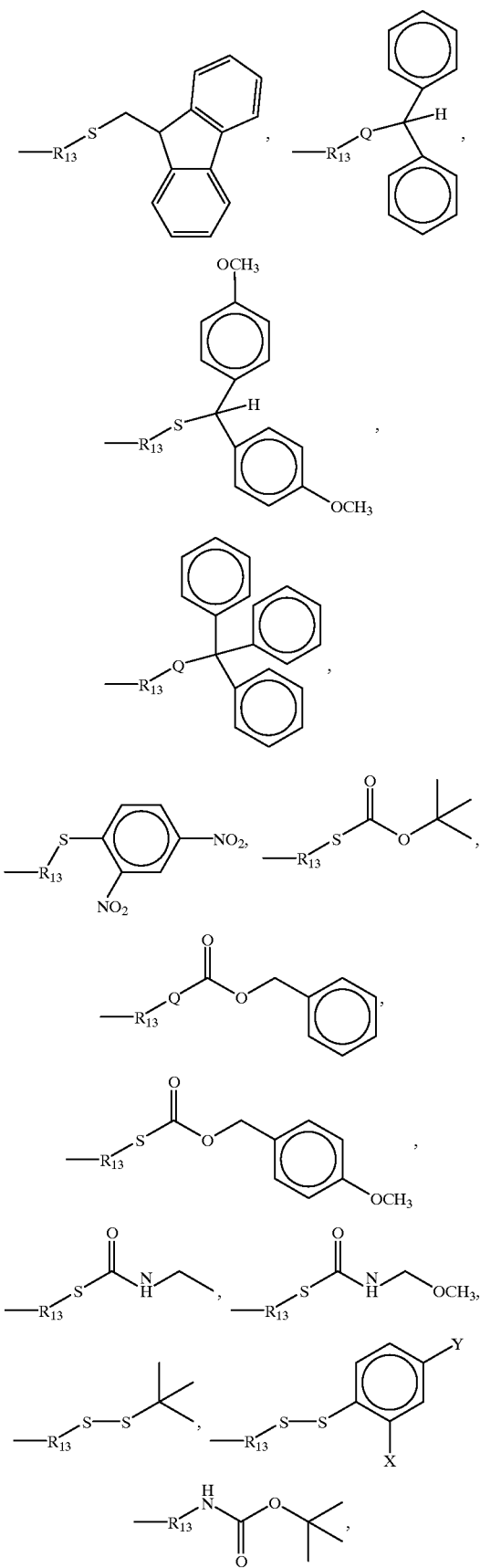

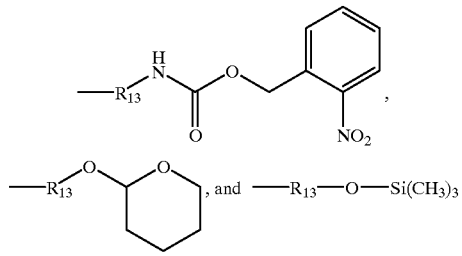

wherein $R_{13}$, $R'_{13}$, $R''_{13}$ and $R'''_3$ are each independently $C_1$–$C_{30}$ alkyl, Q is sulfur, nitrogen-hydrogen or oxygen, X is a halogen and Y is a halogen.

2. The compound of claim 1 wherein $R_{13}$ comprises more than two carbon atoms.

3. The compound of claim 1 wherein at least two adjacent R groups of $R_1$–$R_4$, $R_9$, $R_9'$, $R_{10}$ and $R_{10}'$ are fused to form a ring structure.

4. The compound of claim 1 wherein at least one of $R_1$–$R_4$, is the $C_0$–$C_4$ alkyl group having the hydrophilic substituent.

5. A compound of the formula:

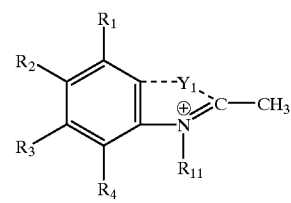

(1)

wherein $Y_1$ is selected from a group consisting of:

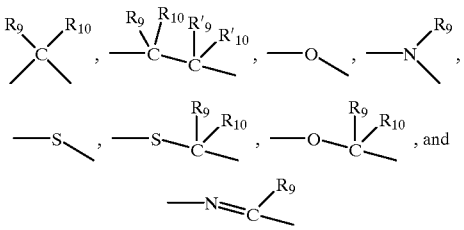

wherein $R_1$, $R_2$, $R_3$, and $R_4$ are each independently selected from a group consisting of: hydrogen, $C_1$–$C_6$ alkyl group, a $C_0$–$C_4$ alkyl group having a hydrophilic substituent selected from a group consisting of sulfonyl, carboxyl, hydroxyl, substituted amines and quaternary amines;

wherein $R_9$, $R_9'$, $R_{10}$ and $R_{10}'$ are each independently selected from a group consisting of $C_1$–$C_{30}$ alkyl, and a heteroatom substituted $C_1$–$C_{30}$ alkyl wherein the heteroatom is O, N or S;

wherein $R_{11}$ is selected from a group consisting of $R_{14}SH$, $R_{14}NH_2$ and $R_{14}OH$; and wherein $R_{14}$ is selected from a group consisting of: $C_3$–$C_{30}$ alkyl and $C_3$–$C_{30}$ alkyl having a phenyl, hydroxyl, sulfonyl, or halogen atom or a heteroatom substituted phenyl.

6. The compound of claim 5 wherein at least one of $R_1$–$R_4$, is the $C_0$–$C_4$ alkyl group having the hydrophilic substituent.

7. The compound of claim 5 wherein at least two adjacent R groups of $R_1$–$R_4$, $R_9$, $R_9'$, $R_{10}$ and $R_{10}'$ are fused to form a ring structure.

8. A process for preparing a compound (1) as claimed in claim 1 which comprises:

reacting a nitrogen containing heterocyclic compound of the formula:

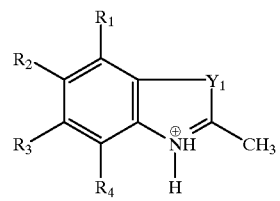

wherein $Y_1$ is selected from a group consisting of:

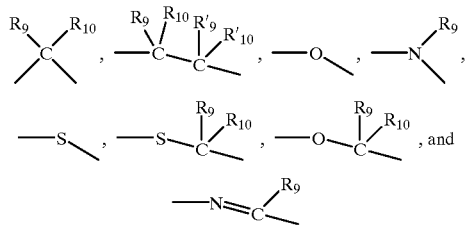

wherein $R_1$, $R_2$, $R_3$, and $R_4$ are each independently selected from a group consisting of hydrogen, $C_1$–$C_6$ alkyl group, a $C_0$–$C_4$ alkyl group having a hydrophilic substituent selected from a group consisting of sulfonyl, carboxyl, hydroxyl, substituted amines and quatenary amines, wherein $R_9$, $R_9'$, $R_{10}$ and $R_{10}'$ are each independently selected from a group consisting of $C_1$–$C_{30}$ alkyl, and a heteroatom substituted $C_1$–$C_{30}$ alkyl wherein the heteroatom is protected O, N or S; and with $XR_{13}Q$ moiety of a bifunctional hydrocarbon wherein X is chlorine, bromine or iodine, $R_{13}$ is $C_1$–$C_{30}$ alkyl and Q is sulfur, nitrogen or oxygen.

9. The process of claim 8 wherein Q is sulfur.

10. The process of claim 8 wherein said bifunctional hydrocarbon is a thiol.

11. The process of claim 8 wherein said bifunctional hydrocarbon is an amine.

12. The process of claim 8 wherein said bifunctional hydrocarbon is an alcohol.

13. A method of treating a neurotransmitter defect or deficiency disorder by using the compound of claim 5 wherein $Y_1$ is

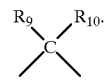

14. The method of claim 13 wherein the compound functions as a mimic of a naturally occurring alkaloid.

15. The method of claim 14 wherein the naturally occurring alkaloid is selected from a group consisting of: Harmaline, Cinchera, Yohimbine, Rauwolfia and Ergot.

* * * * *

UNITED STATES PATENT AND TRADEMARK OFFICE
CERTIFICATE OF CORRECTION

| | | |
|---|---|---|
| PATENT NO. | : 6,114,350 | Page 1 of 1 |
| APPLICATION NO. | : 09/294678 | |
| DATED | : September 5, 2000 | |
| INVENTOR(S) | : Randall et al. | |

It is certified that error appears in the above-identified patent and that said Letters Patent is hereby corrected as shown below:

The error is identified by the printed patent excluding from claim 1, col. 17, line 65 to claim 1, col. 18, line 1 the following:

wherein $R_1$, $R_2$, $R_3$, and $R_4$ are each independently selected from a group consisting of hydrogen, $C_1$-$C_6$ alkyl group, a $C_0$-$C_4$ alkyl group having a hydrophilic substituent selected from a group consisting of sulfonyl, carboxyl, hydroxyl, substituted amines and quaternary amines;

wherein $R_9$, $R_9'$, $R_{10}$ and $R_{10}'$ are each independently selected from a group consisting of $C_1$-$C_{30}$ alkyl, and a heteroatom substituted $C_1$-$C_{30}$ alkyl wherein the heteroatom is O, N or S; and Signed and Sealed this
Sixth Day of September, 2011

David J. Kappos
*Director of the United States Patent and Trademark Office*